United States Patent [19]
Thomas et al.

[11] Patent Number: 6,161,422
[45] Date of Patent: Dec. 19, 2000

[54] SAND TESTING METHOD AND APPARATUS

[75] Inventors: Perry L. Thomas, Fremont; Ronald W. Roethlisberger, Seymour, both of Wis.

[73] Assignee: Hartley Controls Corporation, Neenah, Wis.

[21] Appl. No.: 09/071,445

[22] Filed: May 1, 1998

Related U.S. Application Data

[63] Continuation-in-part of application No. PCT/US96/17387, Nov. 1, 1996.
[60] Provisional application No. 60/007,235, Nov. 3, 1995, abandoned, and provisional application No. 60/015,848, Apr. 19, 1996, abandoned.

[51] Int. Cl.[7] ............................. G01N 15/08; G01N 3/10; G01N 22/04
[52] U.S. Cl. ................................... 73/38; 73/73; 73/790; 73/856; 324/640
[58] Field of Search .................................. 73/38, 73, 84, 73/784, 790, 818, 823, 825, 856, 866; 324/640, 643

[56] References Cited

U.S. PATENT DOCUMENTS

| | | |
|---|---|---|
| 2,791,120 | 5/1957 | Dietert et al. ................................ 73/73 |
| 3,050,992 | 8/1962 | Steinmueller et al. . |
| 3,172,285 | 3/1965 | Dietert et al. ................................ 73/38 |
| 3,638,478 | 2/1972 | Dietert et al. ................................ 73/73 |
| 4,699,011 | 10/1987 | Bradway et al. ......................... 73/823 |
| 4,930,354 | 6/1990 | Knopp et al. ............................ 73/823 |
| 5,724,257 | 3/1998 | Gerosa et al. ............................. 73/73 |
| 5,736,632 | 4/1998 | Nishida et al. ............................ 73/38 |
| 5,756,907 | 5/1998 | Senda et al. ............................. 73/866 |

*Primary Examiner*—Michael Brock
*Attorney, Agent, or Firm*—Thomas D. Wilhelm; Jerry F. Janssen

[57] ABSTRACT

An apparatus (10) and methods for testing the quality of foundry green sand. The apparatus includes three testing stations where filling (60), compaction (80), weighting (94), gas permeability testing (120), moisture testing (40), fracture testing (160), and shear testing (180) occur. Each station is automated and controlled by a computer programmed control system or controller (200). Known foundry sand testing formulas are entered into the system or controller which in turn receives input from each of the testing stations. The condition and quality of the foundry sand is output. A method for testing is also disclosed.

34 Claims, 10 Drawing Sheets

Microfiche Appendix Included
(1 Microfiche, 58 Pages)

SAND TESTING METHOD AND APPARATUS

CROSS-REFERENCE TO RELATED APPLICATIONS

This application is a continuation-in-part of application PCT/US96/17387 filed Nov. 1, 1996 which claims priority to provisional applications Serial Nos. 60/007,235 filed Nov. 3, 1995 and 60/015,848 filed Apr. 19, 1996, both now abandoned.

REFERENCE TO MICROFICHE APPENDIX

This application includes a microfiche appendix (1 of 1) containing 58 pages of computer program listing relating to this invention.

BACKGROUND OF THE INVENTION

This invention relates generally to granular material testing structures and methods and refers more specifically to an automatic structure for performing a plurality of tests for foundry sand including determining the compactability and moisture content of a sample of foundry sand. It is a further development of the inventions of U.S. Pat. Nos. 4,699,011 and 4,930,354. This invention provides a more comprehensive device to more fully automate sand testing.

SUMMARY OF THE INVENTION

A granular material testing apparatus is disclosed comprising three operating stations, a green sand cylinder, and a computer program control system. The green sand cylinder is mounted to a rail structure. A load cell, and a spring, are located underneath the green sand cylinder. The computer program control controls the various tests performed, interprets the data resulting from each test, and provides foundry personnel with a print out of the condition of the sand. The invention provides automated testing apparatus which performs standard tests using standard test methods. The computer program of the control system is used to control and conduct the various tests on the sand.

At the first test station, the green sand cylinder is filled by a funnel filling mechanism, also known as a riddle, to an overflowing condition with green sand, also known as wet sand. At the bottom of the green sand cylinder is a piston mechanism which includes a spring and a load cell.

After the green sand cylinder is filled to overflowing, the control program causes the green sand cylinder to be moved along the rail so that the green sand cylinder passes under an excess sand wiper which removes the excess sand so that the green sand cylinder is completely filled top to bottom and there is now a known volume of sand in the cylinder. The cylinder continues to move from the excess sand wiper, until the cylinder reaches the green sand compacting station.

At the green sand compacting station, the green sand cylinder is positioned under a compacting cylinder, the cylinder powering a piston mounted therein. The piston from the compacting cylinder is extended into the green sand cylinder, thereby compacting the sand. The piston is extended at a known or predetermined pressure. The piston stops extending when the resistance of the sand to compaction is equal to the predetermined extension pressure of the piston. The compaction of the sand is determined by measuring the amount of linear extension of the piston into the green sand cylinder.

During compaction, a significant amount of pressure is applied to the sand within the green sand cylinder and through the sand to the bottom of the green sand cylinder. As previously noted, a load cell is located under the bottom of the green sand cylinder. The load cell has a maximum load capacity which is typically less than the force or pressure applied to the sand during the compaction step. To prevent damage to the load cell during compaction, a spring is positioned under the bottom of the green sand cylinder, between the bottom of the green sand cylinder and the load cell. The spring, based upon the probable maximum pressure which could be produced during compaction, deflects sufficient pressure to prevent damage to the load cell. Springs of different k value may be used to obtain a wide range of corresponding amounts of deflection.

After compaction of the green sand sample, the green sand compaction piston is retracted, and the gross mass of the cylinder and the sand is determined by allowing the cylinder to float freely on the load cell. The mass of the empty cylinder is a known quantity. Accordingly, the difference between the mass of the cylinder empty and the mass of the cylinder full is the mass of the sand. An electrical signal representing the mass of the sand is input into the computer programmed control system and is factored into the equations used to provide necessary information regarding the sand.

After the mass of the sand has been determined, the sample of compacted green sand in the green sand cylinder is raised approximately 0.5 inches (1.27 centimeters) in the green sand cylinder by extending the piston located beneath the green sand cylinder. The piston is then retracted. The bottom of the green sand cylinder is now open to the atmosphere. Accordingly, the entire bottom surface of the compacted green sand sample is exposed to atmospheric air pressure.

At this point, a compacted green sand gas permeability test is performed. After the green sand compression piston has been retracted, a sealing plate is mechanically positioned over the top of the green sand cylinder. The plate is placed on top of the green sand cylinder and the compaction piston is again extended to press the sealing plate against the top of the green sand testing cylinder. Pressing the sealing plate against the top of the green sand testing cylinder prevents air from escaping through the top opening of the green sand testing cylinder. Accordingly, the only exit for air from the green sand cylinder at this time is through the sample and out the bottom of the cylinder, the bottom of the cylinder being open to the atmosphere. With the sealing plate in place, gas is supplied to the top portion of the cylinder above the compacted green sand sample, at a fixed and known, optionally a predetermined, pressure. The rate at which the pressurized gas passes, from the top of the green sand sample, through the green sand sample, and to the bottom of the green sand sample, is measured.

While it is preferred that the green sand sample be raised in the green sand cylinder so that the entire bottom surface is exposed to atmospheric air pressure, the present invention can be practiced with less than the entire bottom surface exposed to atmospheric pressure by introducing a suitable calibration constant into the permeability equation.

At the end of the gas permeability test, the gas is turned off, the green sand compaction piston is retracted, and the sealing plate is removed from the top of the green sand cylinder. The green sand cylinder containing the sample is then moved to the green sand compression strength and moisture testing station. At this station, a predetermined portion of the compacted green sand sample is extruded from the cylinder by extending the piston located beneath the green sand cylinder so that the predetermined portion of the sample is positioned in front of at least one microwave projector. It should be noted that a single microwave projector capable of performing in a manner which provides a result equivalent to the microwave projectors disclosed in the detailed description may be used. A microwave signal is projected to the extruded portion of the green sand sample. Moisture in the sample absorbs microwave energy from the microwave signal. Such absorption of the microwave energy attenuates the microwave signal (i.e. reduces the signal amplitude). The amount of the attenuation is related to the amount of water in the sample. The amount of attenuation is recorded in the computer, and is reported as a moisture level number based upon the formula disclosed below in the program controlling the apparatus.

After the moisture level test, either a green sand shear test or a green sand compression test may be performed. If the shear test is desired, a shear test piston contacts the side of the extruded sample. Again pressure is increased until the sample is sheared and destroyed. The result is recorded by the computer.

Alternatively, the green sand compression test, also known as the strength test, may be performed. In the green sand compression test, a green sand compression piston as at 86 is placed on the top surface of the extruded sample, and is used to apply downward pressure to thereby deform the sample. This deformation is measured in real time by a linear transducer, which measures the displacement of the cylinder or the piston as the piston deforms the sample. The measured displacement is used as a proxy for the displacement, and thus the deformation, of the sample sand plug when the deforming pressure is applied. Consequently, the deformation characteristics of the sample are measured in real time, while the sample is under pressure and before the sample fractures at the green strength limit.

Additionally, the linear transducer may be used to measure the height of the sand plug (the compacted green sand sample) to within plus or minus 0.0002 inches (0.000508 centimeters). The linear transducer may be used to do this in one of at least two ways. The first way includes having a separate linear transducer connected to the piston which is located beneath the green sand cylinder so that, as the predetermined portion of the sample is extruded from the cylinder, the extension of the piston located beneath the green sand cylinder is measured and controlled thereby to extrude only two inches (5.08 centimeters) of the green sand sample plug.

Alternatively, the linear transducer connected to the green sand compression piston may be used where the piston head to which the linear transducer is connected is placed on the top opening of the green sand cylinder and this position is noted via the linear transducer in a computer program. The piston head is held in this position either by gravity or with just sufficient retractive force that, while the piston head is not lifted away from the opening, its effective weight is relatively small. As the sample is extruded, the piston head is lifted by the sample, and the linear transducer continuously communicates to the computer program the distance the sample has been extruded by constantly recording the relative position of the piston head. This information is continuously fed into the computer. The computer causes a signal to be sent to the green sand cylinder when the data supplied by the linear transducer indicates that the top of the sample is two inches (5.08 centimeters) above the top of the sample cylinder.

A third alternative is to use two linear transducers. The first linear transducer is connected to the cylinder head which is above the green sand sample cylinder. The second linear transducer is connected to the piston which is in the green sand cylinder. Both linear transducers are used simultaneously as previously described above to measure the amount of sample extruded.

With the cylinder head in contact with the top of the green sand sample, the linear transducer continuously measures the relative deformation of the sample as the underlying piston is extended, with corresponding increase in pressure within the cylinder head until final deformation or fracture of the sample. Such set-up and operation of the linear transducer in cooperation with the overlying cylinder head enables constant monitoring of the deformation and rate of deformation of the sample so that a distinction may be drawn between deformation and sample fracture.

Alternatively, or additionally, the linear transducer of the present invention can be used to test modulated compressive strength of the sample. In such test, extension of the piston is modulated such that initial pressure is repeatedly applied to the green sand sample, and then released, thereby repeatedly measuring the elastic reaction of the sand sample plug in real time by measuring the springiness or expansion of the sample after compression of the modulated application of pressure to the sample plug. Such modulated compressive force is used to evaluate the elastic properties of the plug by repeatedly applying and releasing the modulated compressive force until there is no longer an elastic restoration or other reaction from the green sand sample.

The information recorded by the linear transducer in real time is communicated in real time to a computer control system. The computer program is capable of producing an output to provide real time information regarding the deformation of the sample prior to fracturing of the sample as well as providing a reading of the size, and changes in size, of the sample.

After compression testing and/or fracture testing is completed, the green sand cylinder is returned to its starting position under the filling station and the remaining sand sample material in the cylinder is discharged so that the cylinder is empty and ready to receive a new sample to be tested.

The present invention is fully automated and simple to operate. The automatic nature of the apparatus increases efficiency and frees the workers to do other work. However, the specific tests can be done using the mechanical apparatus only, independent of the computer program control. Accordingly, practicing the present invention is not dependent upon using the unique structures and methods disclosed herein only in conjunction with the computer program. The use of the computer control program is preferred because it increases the speed of the testing to a level that is faster than the tests could be performed manually. These and other benefits will become evident to those skilled in the art from the following descriptions.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the spirit of the invention which is defined by the claims.

The present invention comprises sand testing apparatus, and methods for testing sand. The invention functions by testing a sample from a batch of foundry green sand. The characteristics and quality of the sand are determined in such testing. The data output is then compared with the desired characteristics and quality level desired in the sand and is used to initiate changes necessary to achieving the optimum foundry green sand, if necessary.

Figure 15:
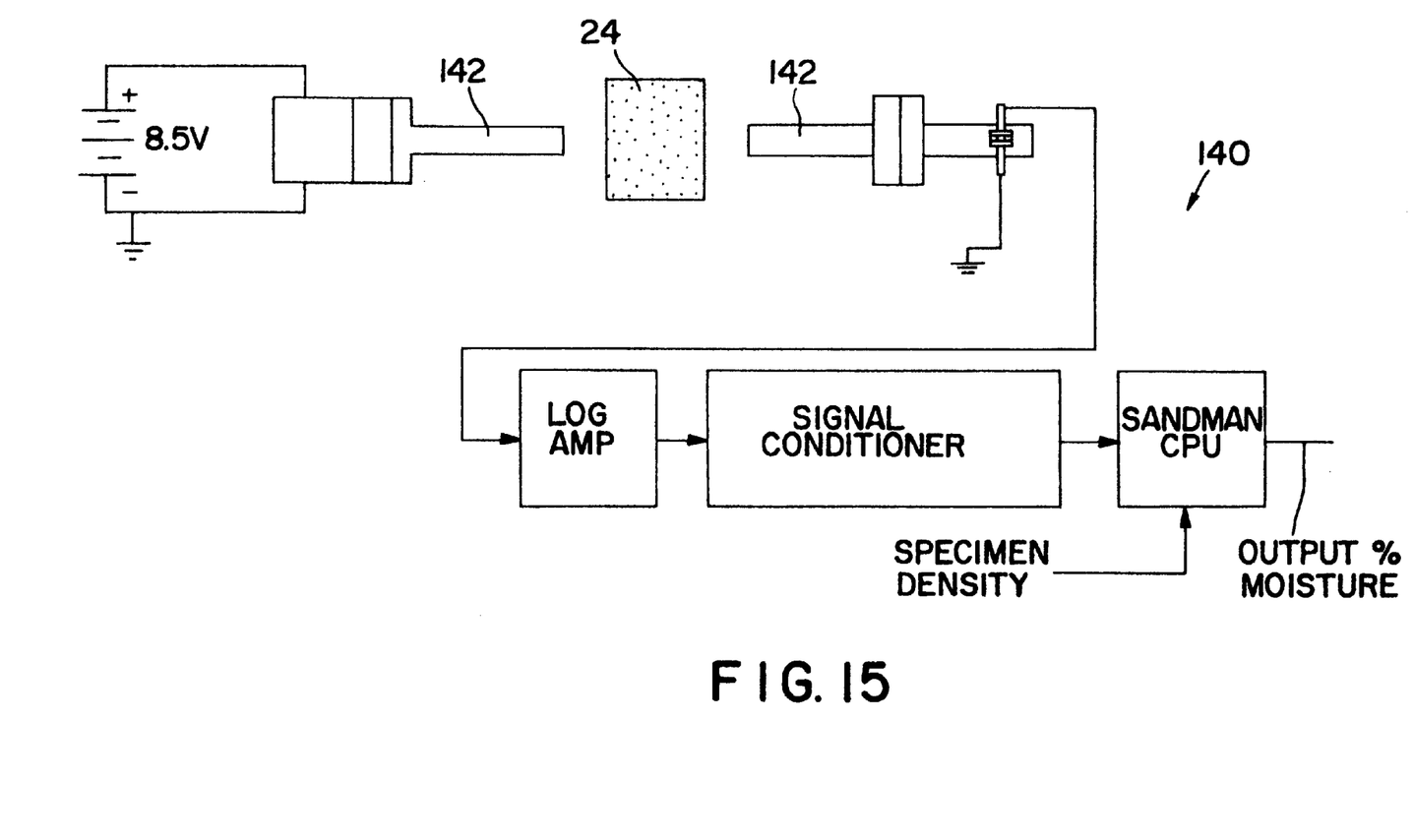
FIG. 15 is a schematic representation of microwave equipment which can be used in sand testing apparatus of the invention.

The invention, and its related structure, are shown generally at sand testing apparatus 10 in the Figures. Sand testing apparatus 10 includes a frame 30, a moving mechanism 40, a sand container 50, a filling station 60, a wiping station 70, a compacting station 80, a moisture testing station 140, a fracture testing station 160 and a shear testing station 180. The sand testing apparatus 10 of the invention can be seen as a whole generally in FIGS. 1, 1A, 13, and 14. Respective ones of the above noted testing stations and their respective components are shown in detail in FIGS. 2 through 12 and 16. FIG. 15 is a representative schematic diagram of moisture testing apparatus which uses microwave projectors.

Figure 1:
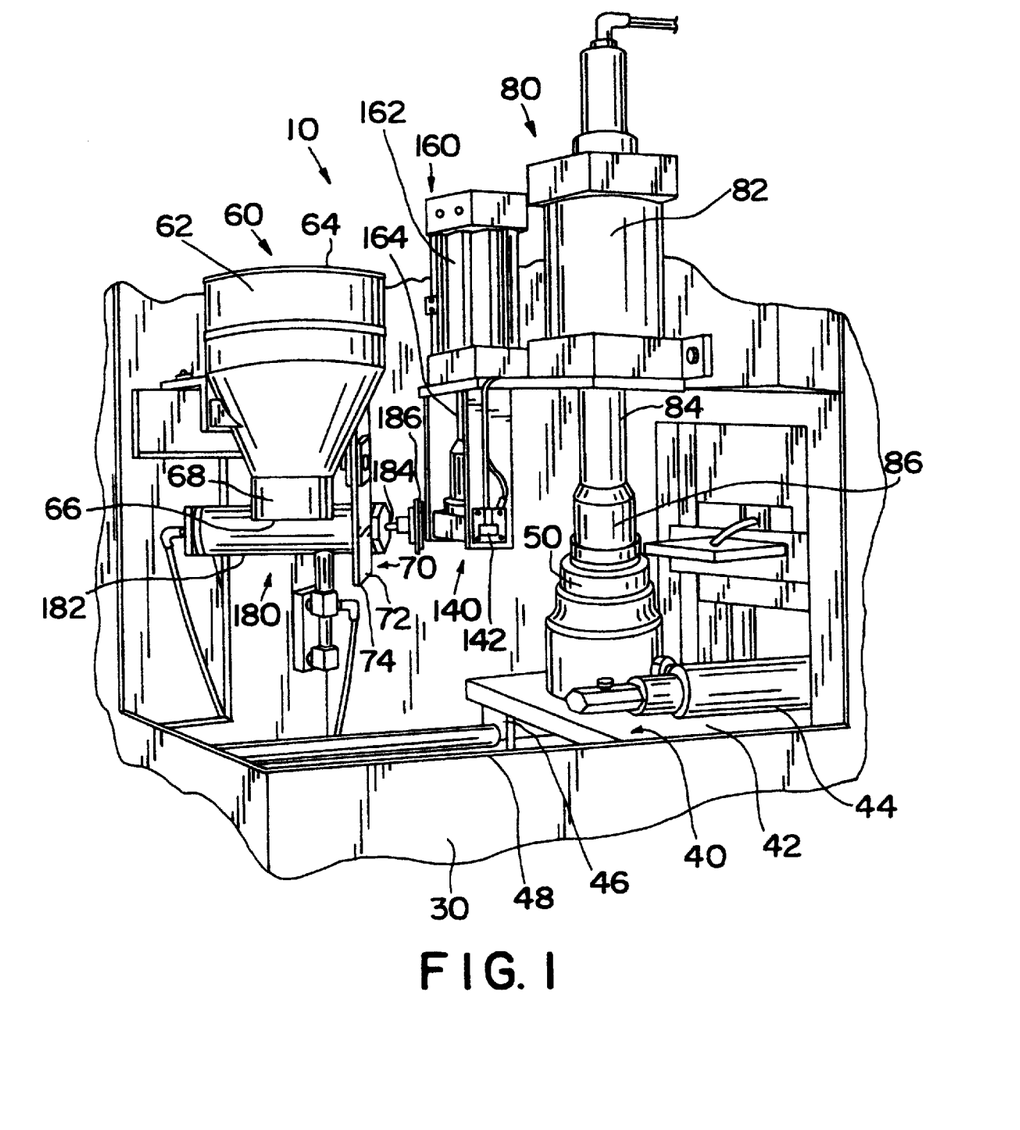
FIG. 1 is a perspective view of sand testing apparatus of the invention.
Figure 1A:
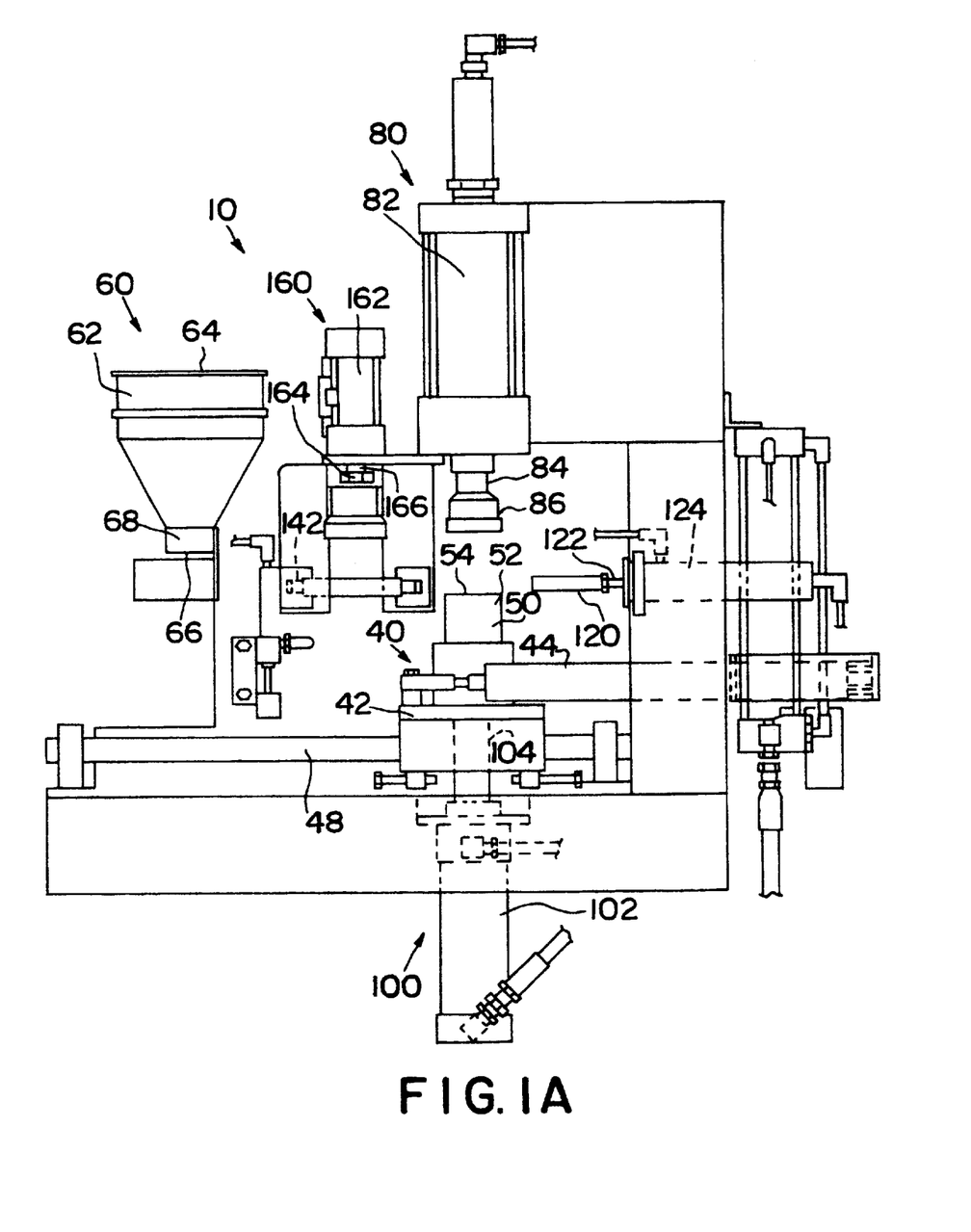
FIG. 1A is a front elevation view of the sand testing apparatus of FIG. 1.

Referring to FIG. 1, a moving mechanism 40 is mounted on frame 30. Moving mechanism 40 includes a table 42, a pneumatic cylinder 44, a pair of table guides 46, and a pair of rails 48, the rails being mounted from frame 30. Table guides 46 are attached to the underside of table 42. Rails 48 pass through table guides 46. When pneumatic cylinder 44 is extended or retracted, table 42 moves along rails 48, accordingly.

Sand container or specimen tube 50 is mounted on table 52. In the preferred embodiment, sand container 50 has a cylindrical interior chamber. However, the interior chamber could comprise any suitable cross-section. Walls 52 of container 50 must be of suitable strength that, when the contents of container 50 are placed under pressure, container 50 will not fracture. Container 50 has an open top 54 and an open bottom 56.

Figure 2:
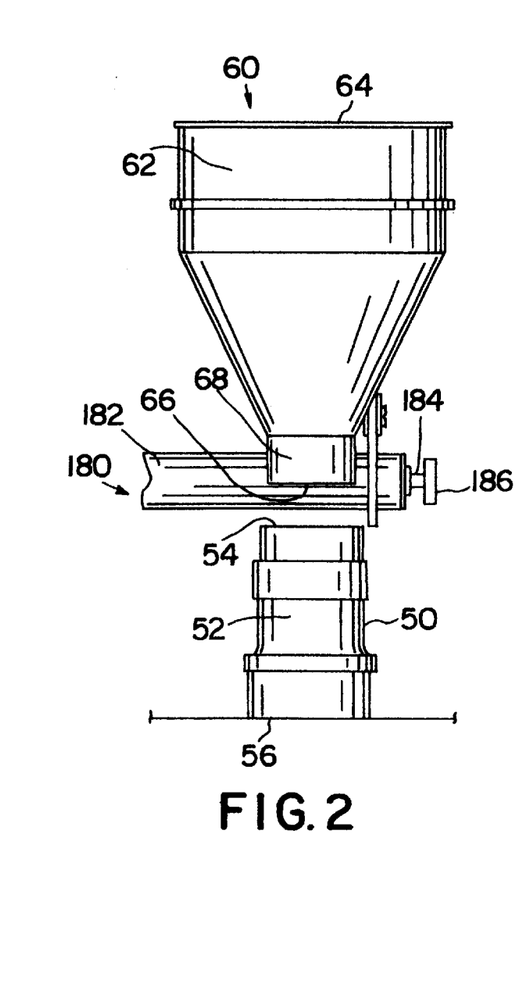
FIG. 2 is a front elevation view of the filling station of the sand testing apparatus of FIG. 1.

Now referring to FIG. 2, filling station 60 of the sand testing apparatus includes a riddle 62 into which green sand to be tested is placed. Riddle 62 has a funnel-like design including an open top 64 and a smaller output chute 66. When container 50 is located at filling station 60, output chute 66 is located directly above open top 54 of container 50. A valve 68 is located in output chute 66. When valve 68 is opened, green sand is dispensed from riddle 62 into container 50. Valve 68 is left open long enough for the sand to fill container 50 to an overflowing condition. Once container 50 has been filled to overflowing with sand, valve 68 is closed.

Next, moving mechanism 40 moves table 42 in a linear direction along rails 48 such that top 54 of container 50 passes under and in wiping contact with wiping station 70. Wiping station 70 comprises a wiping blade 72 having a wiping edge 74. Wiping edge 74 comes within substantial wiping contact with top 54 of container 50. Thus, that portion of the green sand which resides above and outside of container 50, when the sand is in the overflowing condition, is wiped off top 54 of container 50 by wiping edge 74 as the container moves past the wiping blade. The wiped-off green sand falls into a collection bin which is located within sand testing apparatus 10 just below filling station 60. Starting with an overflowing sand condition, and wiping off the overflowing portion of the sand, assures the reliability of each test performed since (a) the amount of sand in the container so will always be of the same volume, and (b) the reliability of the tests depends generally on consistency of the volume from test to test.

Container 50 is permanently mounted to moving mechanism 40. As moving mechanism 40 continues to move table 42, container 50 moves to a second position directly beneath compacting station 80. FIG. 1 shows container 50 in compacting station 80.

When container 50 reaches the second position, moving mechanism 40 stops the table. At compacting station 80, sand container 50 is located directly beneath compacting cylinder 82. Compacting cylinder 82 includes a cylinder ram 84 and a compacting tool 86. Compacting tool 86 is located at the end of cylinder ram 84. Cylinder ram 84 and compacting tool 86 are then extended downwardly from compacting cylinder 82 and into container 50. As compacting tool 86 enters container 50, the sand is compacted into a sand sample 20. Cylinder ram 84 and compacting tool 86 stop extending, and thus reach their most-fully-extended position, when the resistance to the compaction, of the sand, is equal to the predetermined extension pressure of compacting cylinder 82. The most-fully-extended position is maintained for a predetermined period of time. The compaction properties of the sand are determined by measuring the distance of linear extension of the compacting tool 86 into sand container 50 at the most-fully-extended position. The pressure of compaction is a constant.

In the preferred embodiment, the specific interior dimensions of the sand container are 4.75 inches (12.06 cm) in height and 2.0 inches (5.08 cm) in diameter. Given the preferred dimensions, if compacting tool 86 extends 2.375 inches (6.03 cm) into container 50, then the compression of the sand is 50%.

Figure 3:
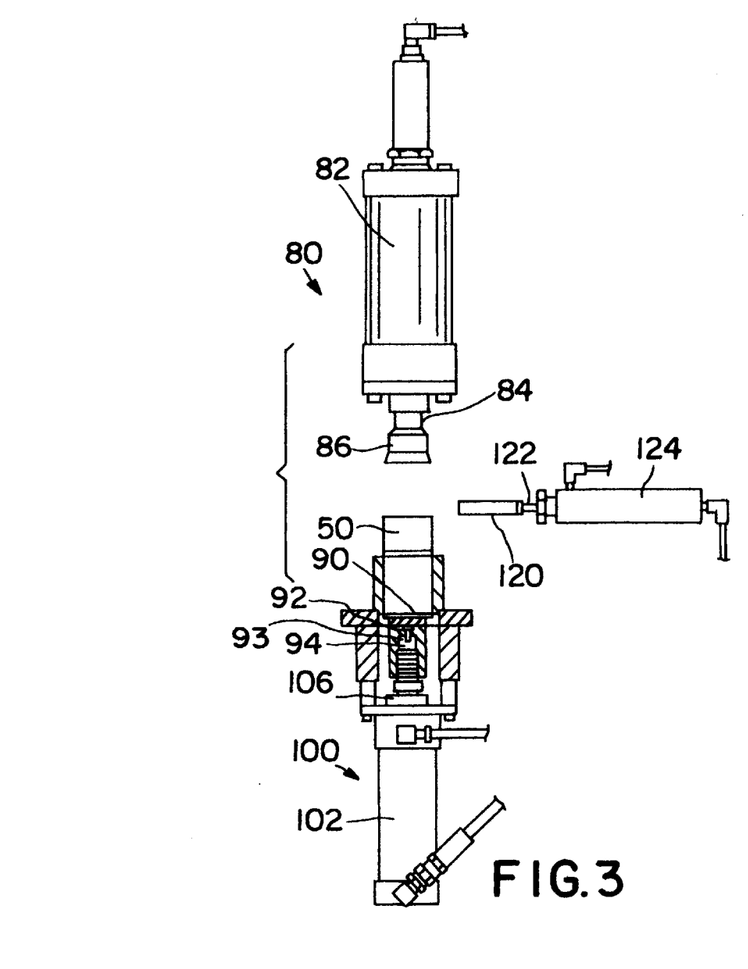
FIG. 3 is a front elevation view of the compacting station of the sand testing apparatus of FIG. 1, including a partial cutaway section of the sand sample raising mechanism.
Figure 4:
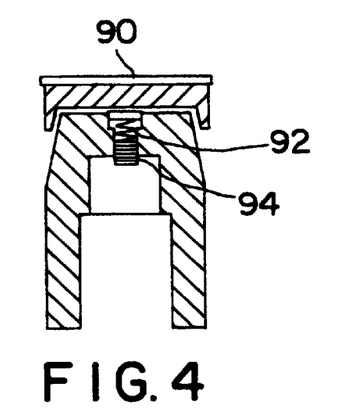
FIG. 4 is a cross-section of a portion of the cutaway section of FIG. 3.

Now referring to FIGS. 3 and 4, it can be seen that container 50 further includes a plate-like floor 90 which fits slidably with container walls 52. Floor plate 90 can be raised and lowered by rod 104 (FIG. 1A) which extends from and retracts e.g. into pneumatic cylinder 102 of raising mechanism 100. Cylinder 102 is mounted on table 42 and extends downward therefrom. Floor plate 90 in turn is supported above raising mechanism 100 by spring 92 and load cell 94. To stabilize load cell 94 and provide a flat surface upon which the load cell rests, a dowel 93 may be inserted between spring 92 and load cell 94. During compaction, a significant amount of pressure is applied to the sand within container 50. The applied pressure passes through the sand to floor plate 90 of sand container 50. Such pressure is initially transferred to load cell 94 which is located beneath bottom plate 90. In the preferred embodiment, load cell 94 has a maximum capacity of 1000 grams. To limit the load applied to load cell 94 during the compression step, spring 92 extends floor plate 90 above piston rod 104 a distance sufficiently great that the sample can be weighed, but sufficiently small that plate 90 abuts the top of piston rod 104 before the force imposed on load cell 94 through spring 92 exceeds the capacity of the load cell. As force is applied to bottom plate 90, the spring deflects as bottom plate 90 is urged downwardly, transferring the load to load cell 94. After plate 90 abuts the top of rod 104, all additional force passes directly from plate 90 to rod 104, whereby the force exerted on the load cell does not exceed the capacity of the load cell. A preferred such spring 92, has a k value of 44 lbs. per inch (19.98 kilograms per 2.54 centimeters).

Figure 5:
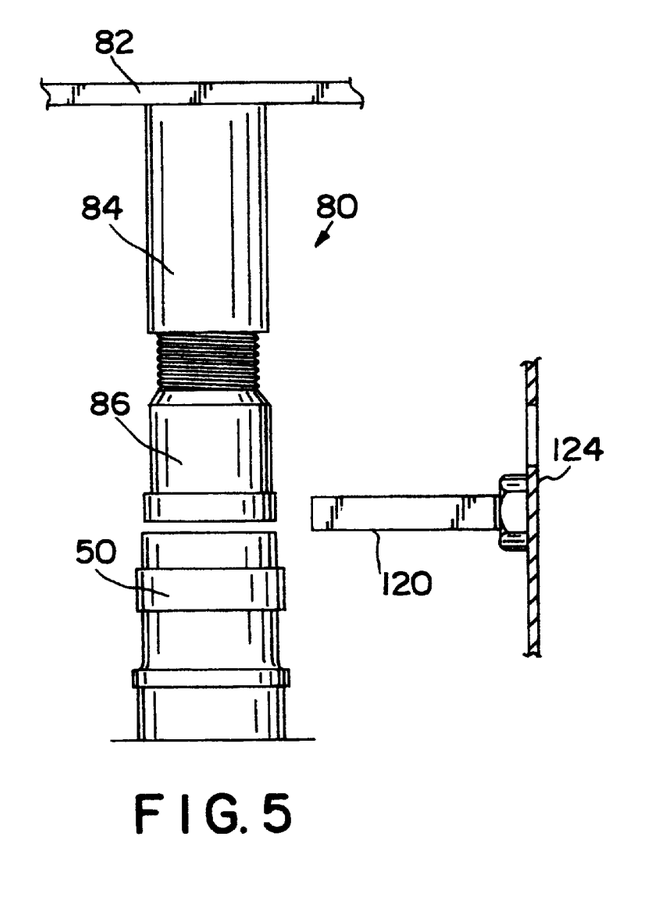
FIG. 5 is a front elevation view of the compacting station of the sand testing apparatus of FIG. 1.

After compacting cylinder 82 completes compaction, compacting cylinder ram 84 and compacting tool 86 are retracted above the top of sand container 50 as shown in FIG. 5. At this point, sand testing apparatus 10 measures the mass of the sand sample 20 in container 50. The combined mass of container 50 and sand sample 20 is determined by allowing the filled container to float freely on the combination of load cell 94 and spring 92. The mass of container 50 is a known quantity. Accordingly, the difference between the mass of the container in an empty state (the above known quantity) and the mass of the container in the filled condition as tested, equals the mass of sand sample 20. The mass of the sand sample 20 is input into controller 200 of the sand testing apparatus 10.

Now referring to FIGS. 6 through 10, a gas permeability test is next performed on sand sample 20. The equation utilized is Permeability=vh/pat where h is the height of the compacted specimen, calculated from the compactability test, p is the pressure head (a constant), a is the specimen area (a constant), and v/t is the air volume flow rate. This equation is found in the American Foundrymen's Association Mold and Core Test Handbook and is incorporated by reference into this specification. This is the accepted industry standard with respect to green sand testing.

The air volume flow rate is measured by a mass flow meter calibrated to read standard liters per minute (SLM). The operating principal of the mass flow meter is based on heat transfer and on conservation of energy. A constant known heat is applied to the air flow stream. Change in temperature of the air flow stream is measured. Since the thermodynamic state and rate of energy addition to the flow stream are known, the rate of mass flow can be calculated. Given the calculated mass flow rate, and assuming standard atmospheric conditions, the volume rate of flow can be calculated by controller 200.

Figure 6:
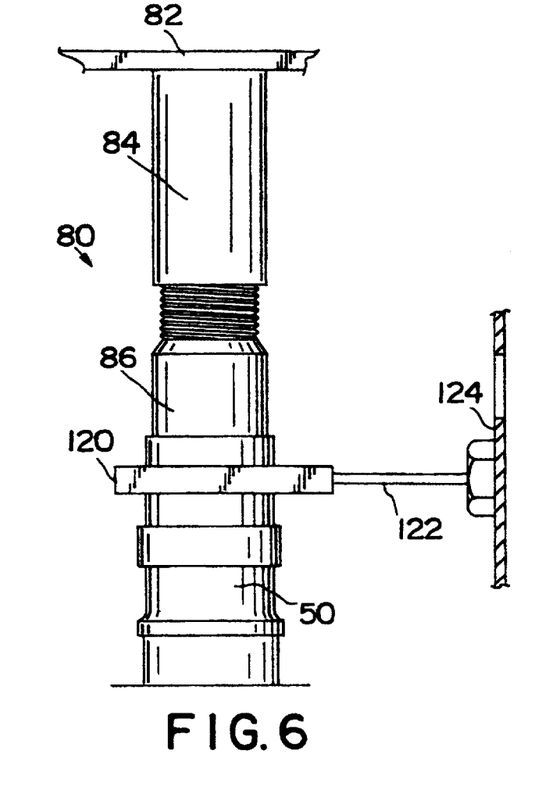
FIG. 6 is a front elevation view of the compacting station of the sand testing apparatus of FIG. 1, showing the sealing plate in position.

Referring specifically to FIG. 6, after compacting tool 86 has retracted a predetermined distance, sealing plate 120 is positioned between compacting tool 86 and container top 54. Sealing plate 120 is connected to sealing plate ram 122 which is in turn connected to sealing plate pneumatic cylinder 124. When cylinder 124 is activated, ram 122 is extended from cylinder 124 and sealing plate 120 is thus moved into position between compacting tool 86 and top 54 of container 50.

Figure 7:
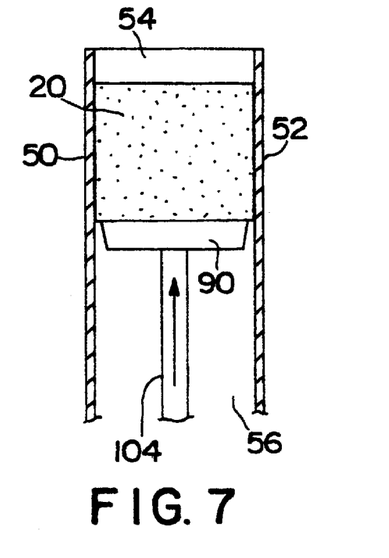
FIG. 7 is a cross-section of the sand container showing the raising piston moving in an upward direction.

FIGS. 3 and 7 show that sample raising mechanism 100 includes pneumatic cylinder 102, cylinder ram 104, and slidable floor plate 90. With sealing plate 120 positioned between compacting tool 86 and container top 54, sand sample 20 is raised approximately 0.5 inch (1.27 cm) in sand container 50, by plate 90.

Figures 8, 9:
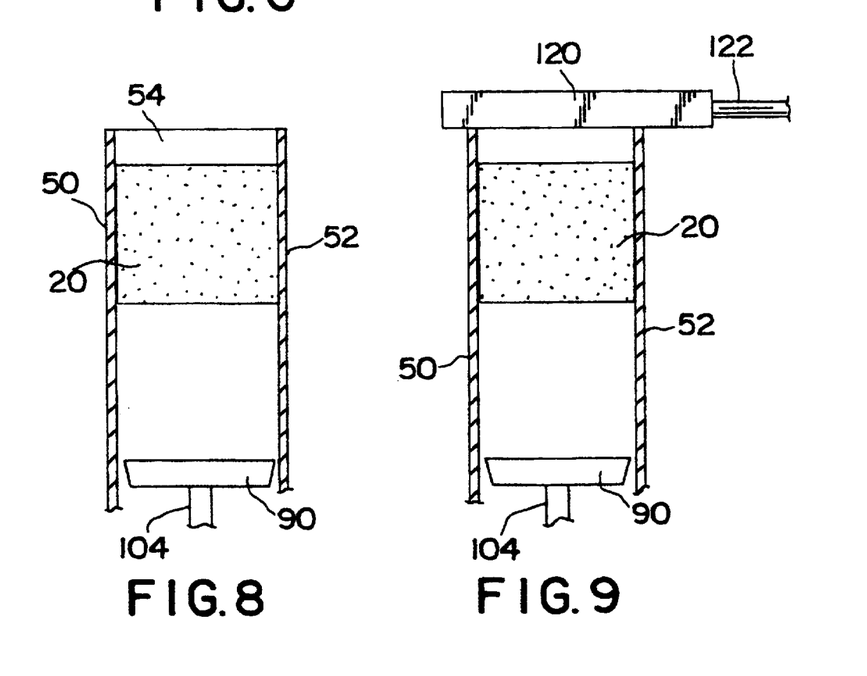
FIG. 8 is a cross-section view of the sand container showing the raising piston in a retracted position.
FIG. 9 is a partially cutaway view of the sand container showing the sealing plate in place on top of the sand container.

Now referring to FIG. 8, plate 90 is retracted from the bottom of sand sample 20 which is still located in sand container 50. When plate 90 is thus retracted, the bottom of sand container 50 is open to the atmosphere. Friction between sample 20 and sidewall 52 of the container holds the sample suspended above bottom plate 90. Accordingly, and given the clearance illustrated in the drawings, between bottom plate 90 and side walls 52, the entire bottom surface of compacted sand sample 20 is exposed to atmospheric air pressure.

Figure 10:
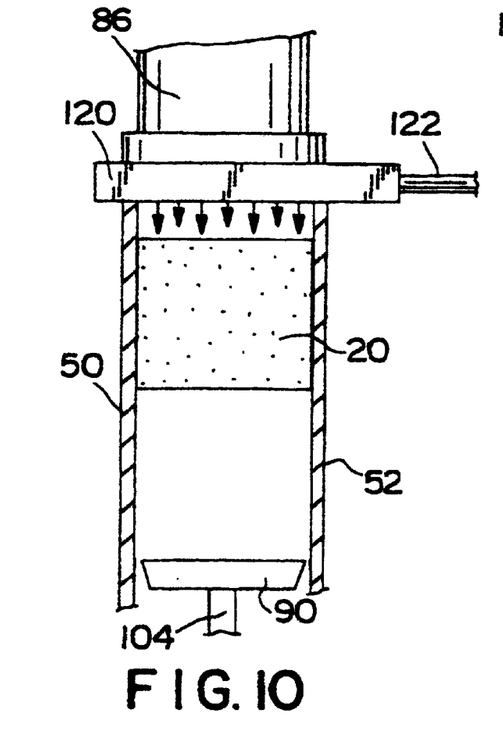
FIG. 10 is a partially cutaway view of the sand container showing the introduction of gas above the sample.

Now referring to FIG. 9, the position of sealing plate 120 covering top 54 of container 50 is shown. As shown in FIG. 10, compacting tool 86 extends downwardly, and urges and thus holds sealing plate 120 in sealed contact with container 50. This closes off any opening between top 54 and compacting tool 86, and thus prevents air from escaping through top 54 of the sand container. Accordingly, the only exit for air from the sand container at this time is from bottom 56 of container 50 which is open to the atmosphere.

As suggested by the arrows in FIG. 10, gas such as air is then supplied to the top portion of container 50 above the compacted sand sample. The gas is supplied at a fixed or known pressure and the rate at which the gas passes from the top of the sand sample, through the sand sample, and to the bottom of the sand sample is measured by the mass flow meter.

While it is preferred that sand sample 20 be raised in container 50 so that the entire bottom surface of the sample is exposed to atmospheric air pressure, it is not necessary that sample 20 be raised to practice this part of the invention. In such event, a calibration constant is introduced into the gas permeability equation utilized by controller 200 to take into account the fact that less than the entire bottom surface area of the sand sample 20 is exposed to atmospheric pressure.

At the end of the gas permeability test, the flow of gas is turned off, compacting tool 86 is retracted, and sealing plate 120 is removed from the top of the sand container.

Moving mechanism 40 is again energized and table 42, to which container 50 is fixedly attached, is moved to the third, sand moisture testing station 140.

Now referring to FIG. 11, cylinder 102 is again energized, whereupon plate 90 is raised a predetermined desired distance, thereby extruding a portion 24 of sand sample 20 approximately 2.0 inches (5.08 cm) above top 54 of sand container 50. The extruded portion 24 is thus raised to a position between a pair of microwave projectors 142. A microwave signal in the frequency range of 10.525 Gigahertz and having a power of 10 milliwatts is projected at the extruded sand sample 24. A MACOM part number MA86751 X Band gun oscillator generates the microwave signal. A MACOM part number 8R22G-5001 Isolator having a range of 10.425–10.625 Gigahertz is mounted to the transmitter to provide protection for the transmitter for any reflected microwaves. A MACOM part number MA86654 X Band horn is attached to a MACOM part number MA86562 X Band sensor that receives the microwave signal. A MACOM part number MA40194 super sensitive Schottky diode is substituted for the standard diode that comes with the MACOM part number MA86562 X Band sensor. The MACOM parts are available from M/A-COM Inc., Burlington, Mass.

Figure 11:
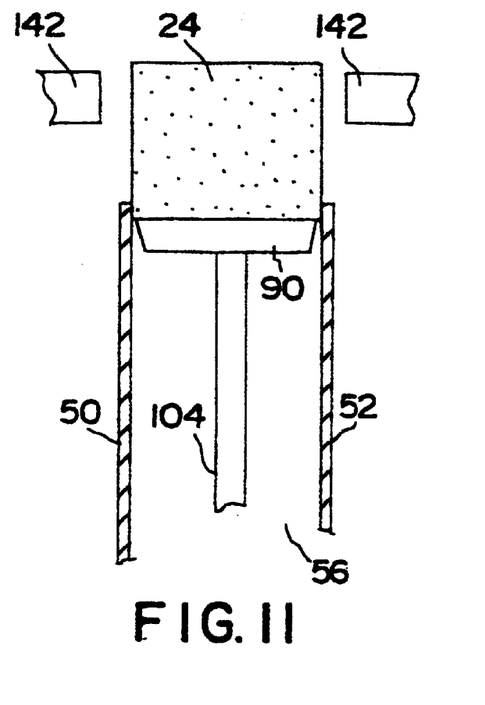
FIG. 11 is a partially cutaway view of the sand container showing the sand sample and microwave projectors.

The moisture in the extruded sand sample is sensitive to the 10.525 Gigahertz frequency. The moisture attenuates the signal being transmitted to the receiver. The attenuated signal is related to the amount of water in extruded sand sample 24.

The Schottky diode converts the microwave signal to an electric signal that is processed through an electronic circuit board to provide a signal to controller 200. Controller 200 uses the signal from the microwave apparatus, and the density (as previously calculated), to finally determine the percentage of moisture in sand sample 24.

Moisture in extruded sample 24 absorbs the microwave energy. Such energy absorption causes attenuation of the microwave signal in relation to the amount of water in extruded sample 24. The amount of moisture so calculated is recorded by controller 200, and is reported as a moisture level amount based upon the above noted relationship utilized by controller 200.

Figure 12:
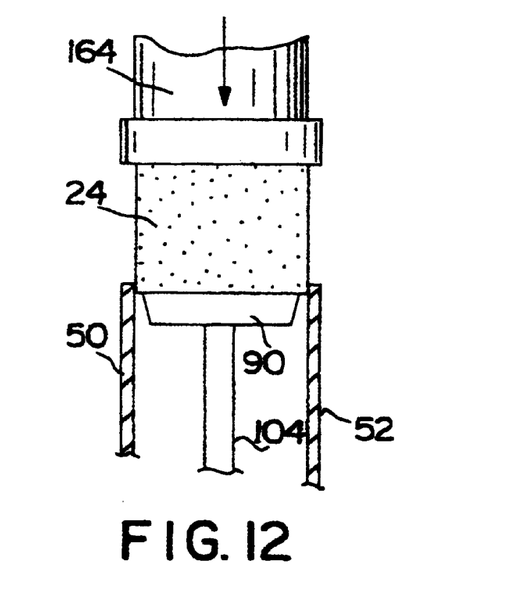
FIG. 12 is a partially cutaway view of the sand container showing the sample and compacting tool just prior to sample destruction.

Next, either the fracture or shear of the extruded sample 24 is measured by sand testing apparatus 10. If the fracturing test is chosen, fracture testing apparatus 160 fractures the extruded sample and records the fracture pressure. Apparatus 160 includes pneumatic cylinder 162 which operates piston 164, pneumatic cylinder 162 being located above microwave projectors 142. With table 42 still located at moisture testing station 140, cylinder 162 is energized and thereby extends piston 164 downwardly toward extruded sample 24. Cylinder 162 continues to extend piston 164 until the piston makes contact with the top surface of extruded sample 24. The pressure in cylinder 162 is then increased until the sample is fractured. This test destroys the sample. The pressure at fracture is recorded by controller 200.

Figure 16:
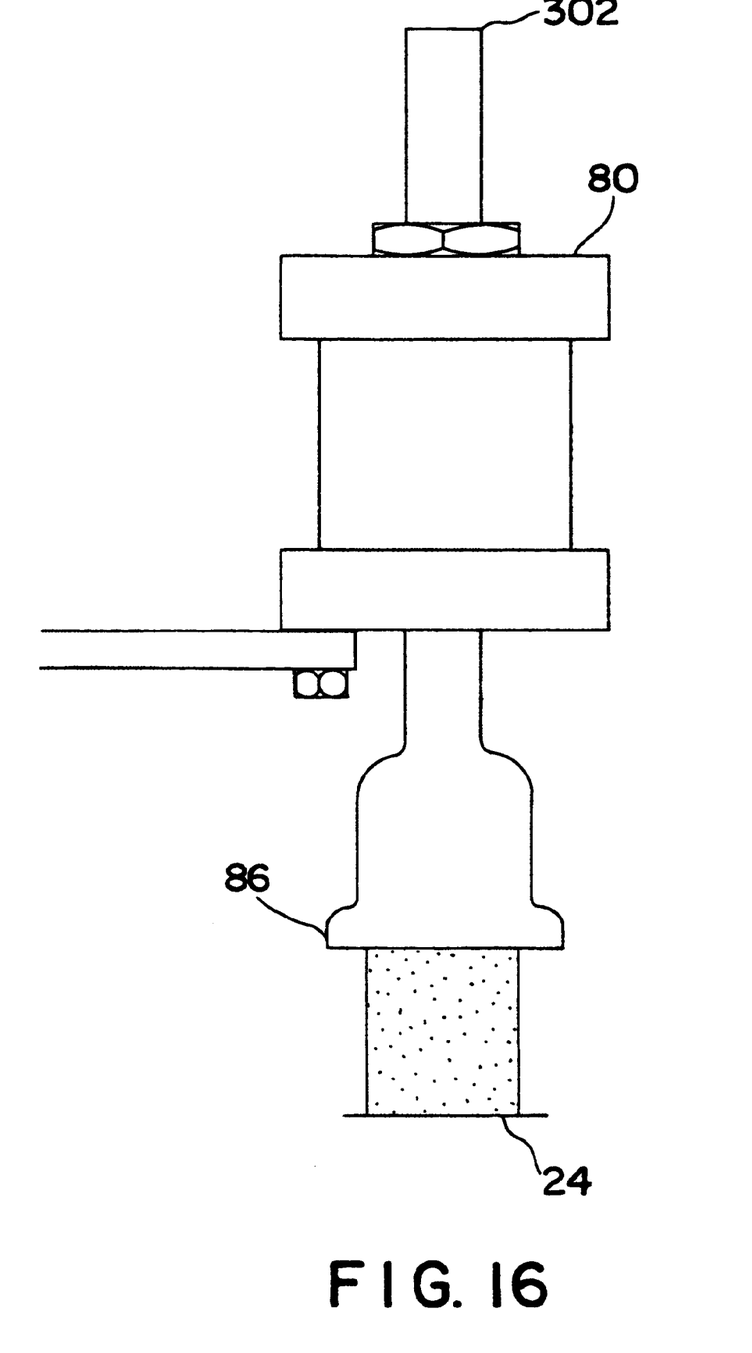
FIG. 16 is a side elevation view of the green strength testing station showing a linear transducer coupled to the station.

Referring to FIG. 16, the green sand compression test can also be performed wherein a green sand compression piston 96 is applied to the top surface of extruded sample 24 and is used to apply downward pressure at the top of the sample while the sample is immovably supported from beneath by plate 90, thereby to deform the sample. This deformation is measured in real time by linear transducer 302, which measures the displacement of the cylinder extension or the piston as the piston deforms the sample. The measured displacement of the cylinder or piston is used as a proxy for the displacement of the top surface of the sand sample 24, and thus as a proxy for the deformation of the sand sample, when the deforming pressure is applied. Consequently, the deformation characteristics of sample 24 are measured in real time, while the sample is under pressure and before the sample fractures at the green strength limit.

Additionally, linear transducer 302 may be used to measure the height of sand plug 24 (the compacted green sand sample) to within plus or minus 0.0002 inch (0.000508 centimeter). Linear transducer 302 may be used to do this in one of at least two ways. The first way includes having a separate linear transducer (not shown) connected to e.g. ram 104 which is located beneath the green sand cylinder so that, as the predetermined portion of the sample is extruded from cylinder 50, the extension of ram 104 from cylinder 102 is measured and controlled so that only two inches (5.08 centimeters) of the green sand sample plug is extruded.

In the second way, linear transducer 302 is connected to e.g. cylinder ram 84. Compression piston 96 is placed on open top 54 of the green sand cylinder 50 and this position is noted via the linear transducer in computer 200.

Compression piston 96 is held in this position either by gravity or with just sufficient retractive force so that while the compression piston is not lifted away from the opening, its effective weight on cylinder 50 is relatively small so that, as the sample is extruded, compression piston 96 is readily lifted by the emerging sand sample 24. Linear transducer 302 continuously communicates to the computer program the relative position of compression piston 96. The relative position of compression piston 96 corresponds with the distance the compression piston has been lifted, which the computer program uses as a proxy for the distance the sample has been extruded above the top of cylinder 50. The information thus collected by linear transducer 302 is thus continuously fed into computer 200. The computer causes a stop signal to be sent to pneumatic cylinder 102 when the position of compression piston 96 is determined, from the data supplied by the linear transducer, to be two inches (5.08 centimeters) above top 54 of sample cylinder 50, whereby two inches (5.08 centimeters) of sample have been extruded from cylinder 50.

A third way is to use two linear transducers, one connected to compression piston 96 above the green sand cylinder and one connected to ram 104 of pneumatic cylinder 102. In this embodiment, the two linear transducers are used simultaneously as previously described above to measure the amount of sample extruded.

Upon contact with the green sand sample by compression piston 96, the relative rates of movement of ram 104 and compression piston 96 are continuously transmitted to computer 200, where the computer computes the deformation of the sample based on the relative movements of ram 104 and compression piston 96, until fracture or other final deformation of the sample occurs. Computer 200 thus constantly monitors the deformation and rate of deformation of the sample so that a distinction may be drawn empirically between deformation and sample fraction.

Linear transducer 302 can also be used in a modulated compression test of a two inch (5.08 centimeter) extruded green sand sample wherein a compressive force is applied by e.g. compression piston 96, and is modulated such that an initial force is applied to green sand sample 24 and then released and then applied again and released again, thereby measuring the elastic reaction of the sand sample plug in real time to multiple applications and releases of force, and recording the respective lengths and changes in length resulting from each application and release of the forces, thus in response to the modulation of the force applied to plug 24. This compressive force is used to determine the limits on the elastic deformation and restoration of the sand sample plug by applying the modulated compressive force until there is no longer a restorative elastic reaction from the green sand sample.

The information recorded by the linear transducer in real time is communicated in real time to the computer control system running a program.

The computer program is capable of producing an output to provide real time information regarding the deformation of the sample prior to fracturing of the sample as well as providing an extremely accurate reading of the size of the sample.

Alternatively, the shear strength of the extruded sample 24 can be measured instead of the above noted deformation and/or fracture strength measurements. Again, table 42 and container 50 remain in position below moisture testing apparatus 140. Shear testing apparatus 180 (FIGS. 1 and 2) includes pneumatic cylinder 182, ram 184, and shear test plate 186. With the extruded sample at the above noted location, ram 184 is extended from cylinder 182 toward the sample until shear test plate 186 makes contact with the side of the sample. The sample then resists further extension of ram 184 and corresponding movement of test plate 186. The pressure required in cylinder 182 is increased until sample 24 is sheared. This test also destroys the sample. The resulting maximum pressure used in cylinder 182 is recorded by controller 200.

Upon completion of all tests to be performed on the sand sample, floor plate 90 is raised to its uppermost position, which is approximately even with top 54 of container 50. Table 42 is then energized and moves to its initial position below filling station 60. As top 54 of container 50 passes wiping station 70, wiping blade 72 removes all sand supported on floor plate 90 and any sand on the top of the cylinder 50. Thus when floor plate 90 subsequently retracts, container 50 will be empty.

Figure 13:
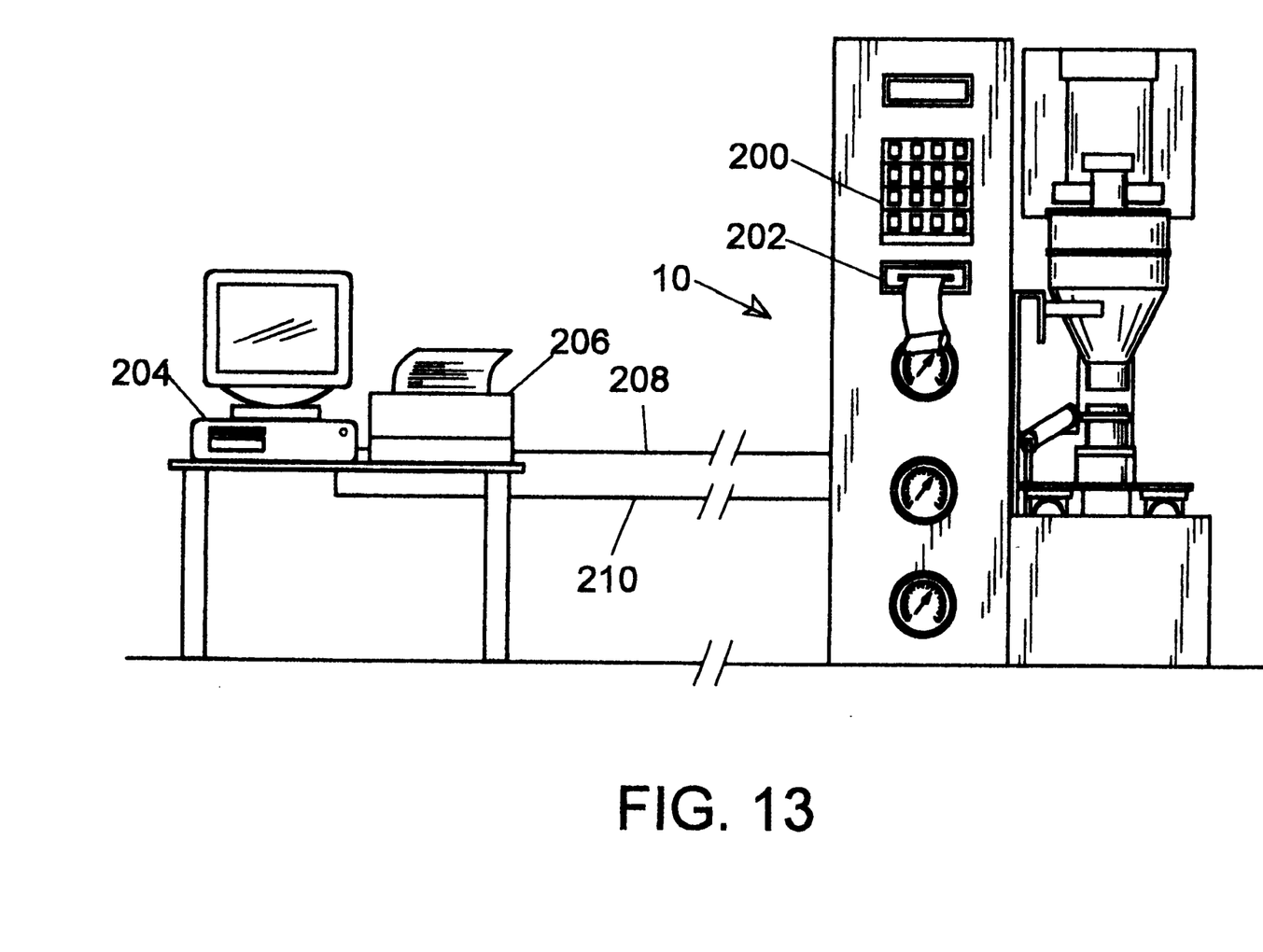
FIG. 13 is a side elevation view of sand testing apparatus of the invention, including the control panel.
Figure 14:
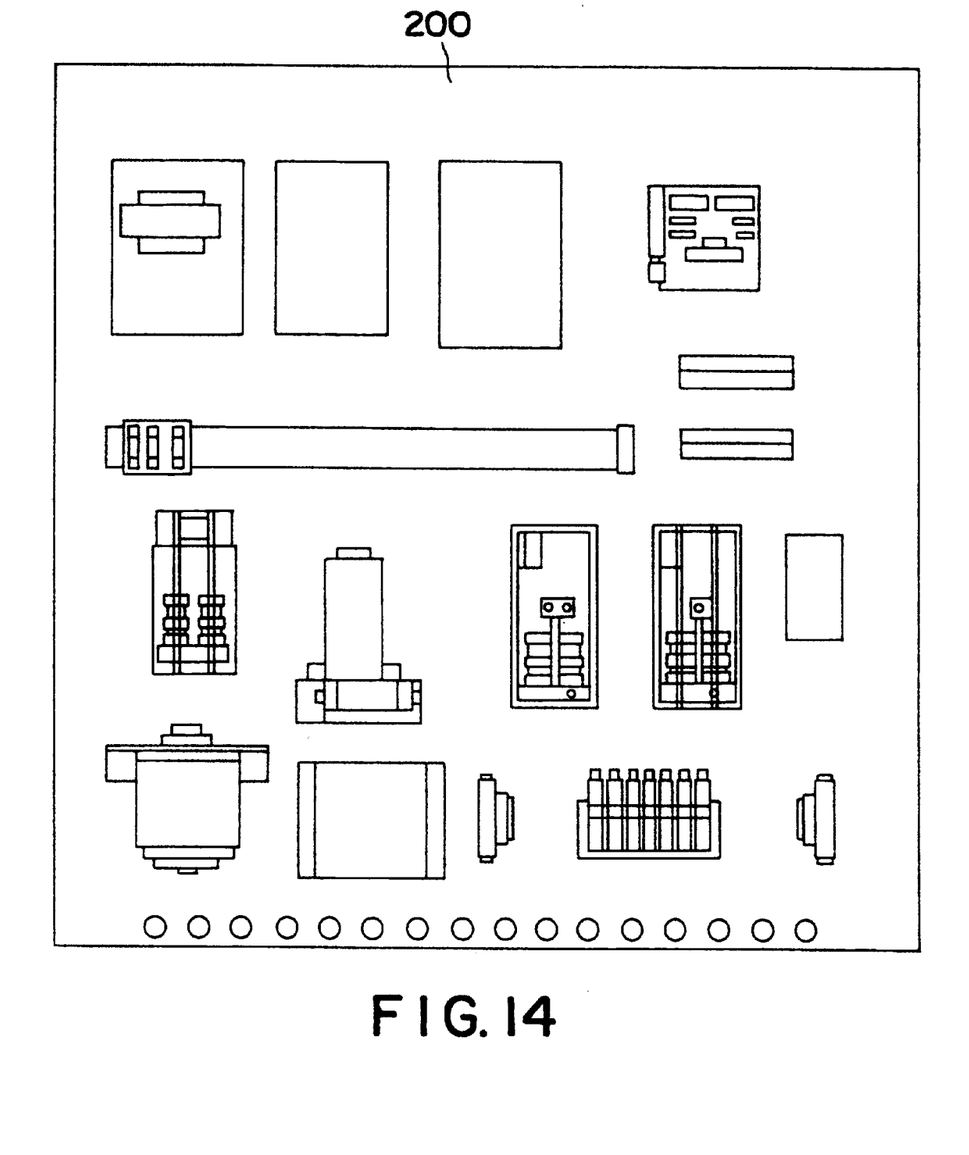
FIG. 14 is a rear elevation view of the back of sand testing apparatus of the invention.

The invention comprehends methods for testing sand. An exemplary method comprises an automated series of coordinated steps including the following steps: agitating granular material with an agitator and thereby sifting the granular material through a screen in the riddle, delivering the granular material to a container or specimen tube, leveling the granular material in the container as the container traverses to the compaction station, compressing the granular material, and thereby measuring compatibility of the material, sensing linear motion of compression in real time, and passing such linear motion information to controller 200, measuring the mass of the granular material and passing such mass information to controller 200, measuring the gas permeability of the granular material and passing such permeability information to controller 200, measuring the moisture content of the granular material and passing such moisture content information to controller 200, measuring either fracture strength or shear strength of the granular material and passing such strength information to controller 200, and outputting results of the above testing of the granular material, from computer 200 as by printed tabulation to a printer. As is shown in FIG. 13, the printer may be mounted in the test apparatus 10 as printer 202, or may be remote from the test apparatus 10 such as 206, communicating directly with the computer 200 in test apparatus 10 through signal line 208 connected to a serial port (not shown) on the test apparatus. Alternatively, a computer 204, such as a personal computer, may be remote from the test apparatus 10, communicating with the test apparatus 10 through signal line 210. In this embodiment, the remote printer receives output from the test apparatus test apparatus through remote computer 204. A third alternative contemplates two printers, a first computer 202 mounted in the test apparatus and a second computer, 206, each communicating with the test apparatus 10 through serial output ports (not shown).

Controller 200 can output the test results through a serial port or a parallel port, or both. Typically, output through a parallel port is fed to a local printer mounted on testing apparatus 10. See FIG. 13. Output through the serial port makes the data available for computer manipulation in various computer apparatus such as a personal computer, or a printer remote from testing apparatus 10. Use in a personal computer can include, for example, electronic storage or mathematical manipulation of the test results.

The illustrated programming language is C. Specifically, the computer program disclosed was made by using a package call MICRO C sold by Dunfield Development Systems of Toronto, Canada.

All the above mentioned apparatus is easily mounted on suitable wheels for easy movement throughout an industrial plant.

The foregoing is considered as illustrative only of the principles of the invention. Since numerous modifications and changes will readily occur to those skilled in the art, the invention is not limited to the exact construction and operation shown and described. While the preferred embodiment has been described, the details may be changed without departing from the invention, which is defined by the claims.

Having thus described the invention, what is claimed is:

1. A testing system for testing bulk particulate material, said testing apparatus comprising:
   (a) a sample cylinder receiving a sample of such bulk particulate material;
   (b) test apparatus associated with said sample cylinder for performing a plurality of tests including weight, permeability, compactibility, deformation, and strength on a given such sample; and
   (c) a control system automatically effecting and controlling performance of such plurality of tests, and outputting results of such tests in a form compatible with computer manipulation of such test results.

2. A testing system as in claim 1, including weight measuring apparatus effective to test a given sample, in addition, for weight, and to use the weight measurement in computing another property of the sample.

3. A testing system as in claim 2, said weight measuring apparatus comprising a load cell aligned with, and exposed to, a force imposed on such sample during compaction.

4. A testing system as in claim 3, said load cell having a maximum capacity less than the maximum force imposed on such sample during compaction.

5. A testing system as in claim 4, including a spring between said load cell and such sample, said spring having an effective deflection length in said testing system operative to enable said load cell to weigh the sample while protecting said load cell from the maximum force imposed on such sample during compaction.

6. A testing system as in claim 4, said testing system further comprising a spring between said load cell and such sample, said spring and said load cell being mounted in a support, a sample receiving table being mounted above said spring and imposing a weight on said spring above said support, said spring retaining said table a sufficient distance above said support to enable weighing a sample on said table, and sufficiently close to said support that, upon application of a force to said table, said table deflects said spring, and moves downwardly into direct contact with said support prior to the deflection in said spring transferring to said load cell a force greater than the maximum capacity of said load cell.

7. A testing system as in claim 6, including a transport vehicle effective to transport said sample cylinder among work stations in said testing system, said load cell being mounted on said transport vehicle.

8. A testing system as in claim 3, said load cell being effective to make an initial determination of weight of such sample after such sample has been compacted.

9. A testing system as in claim 3, including a transport vehicle effective to transport said sample cylinder among work stations in said testing system, said load cell being mounted on said transport vehicle.

10. A testing system as in claim 1, said testing system including sensors effective to determine the length of such sample, the length of such sample being a variable from sample-to-sample, and further comprising air permeability measuring apparatus effective to feed air through such sample under pressure and to compute air permeability of such sample using the equation $$P=vh/pat$$

where
P=Air permeability
v=volume of air flow through the sample
h=height of the sample
p=pressure head
a=the sample area
t=time over which air flow is being measured.

11. A testing system as in claim 1, said sample cylinder having a top and a bottom, said testing system further comprising air permeability measuring apparatus effective to feed air downward from the top of said sample cylinder through such sample and toward the bottom of said sample cylinder while the sample is in said cylinder.

12. A testing apparatus as in claim 1 including means for compacting said sample, means for extruding a portion of said compacted sample from said sample cylinder, and microwave apparatus using microwave energy to determine the moisture content of the extruded portion of such sample.

13. A testing system as in claim 1, including a printer mounted in said test apparatus.

14. A testing system as in claim 1, said control system including a serial output, and computer apparatus receiving such serial output.

15. A testing system as in claim 14, said computer apparatus comprising a personal computer remote from said test apparatus.

16. A testing system as in claim 14, said computer apparatus comprising a printer remote from said test apparatus.

17. A testing system as in claim 1, including a first output port, a first local printer being connected to said first output port, and a second output port, said second output port being a serial port, a second printer being connected to said second output port and being disposed at a location remote from said test apparatus.

18. A testing system as in claim 1, said control system including a serial output outputting results of such tests.

19. A testing system for testing bulk particulate material, said testing system comprising:
(a) a sample cylinder receiving a sample of such bulk particulate material;
(b) test apparatus, associated with said sample cylinder, for compacting such sample and performing a plurality of tests on a given such sample, including weight measuring apparatus measuring weight of such compacted sample.

20. A testing system as in claim 19, further comprising a control system automatically effecting and controlling performance of such plurality of tests.

21. A testing system as in claim 19, said weight measuring apparatus comprising a load cell aligned with, and exposed to, a force imposed on such sample during compaction.

22. A testing system as in claim 21, said load cell having a maximum capacity less than the maximum force imposed on such sample during compaction.

23. A testing system as in claim 21, said testing system further comprising a spring between said load cell and such sample, said spring and said load cell being mounted in a support, a sample receiving table being mounted above said spring and imposing a weight on said spring above said support, said spring retaining said table a sufficient distance above said support to enable weighing a sample on said table, and sufficiently close to said support that, upon application of a force to said table, said table deflects said spring, and moves downwardly into direct contact with said support prior to the deflection in said spring transferring to said load cell a force greater than the maximum capacity of said load cell.

24. A testing system as in claim 19, said weight measuring apparatus being constructed and configured to make an initial measurement of weight of such sample after such sample has been compacted.

25. A testing system as in claim 19, including microwave apparatus using microwave energy to determine moisture content of such sample.

26. A testing system as in claim 19, including a control system automatically effecting and controlling performance of such plurality of tests, and outputting results of such tests in a form compatible with digital manipulation thereby to use the weight of such sample in determining other physical properties of such sample.

27. A testing system as in claim 26, said control system including a serial output outputting results of such tests.

28. A testing system for testing bulk particulate material comprising a sample container for receiving a sample of said bulk particulate material, and testing apparatus associated with said sample container for carrying out a plurality of tests on said sample, the testing apparatus comprising:
(a) apparatus for compacting said sample of bulk particulate material in said container to form a compacted sample;
(b) apparatus for weighing said compacted sample;
(c) apparatus for determining the length of said compacted sample; and
(d) apparatus for feeding air under constant pressure through said compacted sample to measure the permeability of said compacted sample.

29. A testing system as in claim 28 wherein air is fed through the entire length of such a sample in determining air permeability.

30. A testing system as in claim 28, including sensing and calculating apparatus determining air permeability on a sample completely contained within said sample cylinder.

31. A testing system as in claim 28, said air permeability measuring apparatus being effective to transport a stream of air flowing therethrough, and to measure mass flow rate of air therethrough for determining air permeability.

32. A testing system as in claim 31, said air permeability measuring apparatus measuring mass flow rate by sensing a temperature change in the air stream.

33. A testing system as in claim 28 further including apparatus for extruding a portion of said compacted sample from said container and microwave apparatus using microwave energy to determine the moisture content of said extruded portion of said compacted sample.

34. A method of measuring the moisture content of compacted sample of particulate material comprising the steps of:

(a) placing an un-compacted sample of particulate material in a sample container, said container having a moveable compacting tool and a floor plate;

(b) compacting said sample in said container under a predetermined load between said moveable compacting tool and said floor plate;

(c) weighing said compacted sample while said sample is contained within said sample container to determine the density of said sample;

(d) withdrawing said compacting tool from said container and moving said floor plate to extrude a portion of said compacted sample from said container; and (e) passing a microwave signal through said extruded portion of said compacted sample to determine the moisture content of said compacted sample based upon the density of said compacted sample and the degree of attenuation of said microwave signal.

* * * * *